United States Patent [19]

Alfranca

[11] Patent Number: 4,617,928
[45] Date of Patent: Oct. 21, 1986

[54] SURGICAL INSTRUMENT FOR PRACTICING MECHANICAL SUTURES AND BIOPSIES

[76] Inventor: José-María P. Alfranca, Santa Teresa, 29-35, esc. 1ª-6º A, 50006 Saragossa, Spain

[21] Appl. No.: 651,610

[22] Filed: Sep. 17, 1984

[51] Int. Cl.⁴ .................. A61B 17/11; A61B 17/32; A61B 17/04
[52] U.S. Cl. .................. 128/305; 128/334 R; 227/19; 227/DIG. 1
[58] Field of Search ........... 128/334 R, 334 C, 305, 128/751, 335; 227/19, DIG. 1

[56] References Cited

U.S. PATENT DOCUMENTS 3,795,034   3/1974   Strekopytov et al. .......... 128/334 R
4,319,576   3/1982   Rothfuss ........................ 128/305

FOREIGN PATENT DOCUMENTS 1835500   4/1961   Fed. Rep. of Germany ... 227/DIG. 1
942122   11/1963   United Kingdom ............ 128/334 R
2119694   11/1983   United Kingdom ............ 128/334 R
762869    9/1980   U.S.S.R. ........................ 128/334 R
1069794   1/1984   U.S.S.R. ........................ 128/334 R Primary Examiner—Richard C. Pinkham
Assistant Examiner—Matthew L. Schneider
Attorney, Agent, or Firm—McGlew and Tuttle

[57] ABSTRACT

A surgical instrument for performing mechanical suturing and biopsies comprises a fixed leg having an upper body defining a channel and a lower head connected to the body and incorporating a suturing mechanism which includes a pusher for pushing a V-shaped arrangement of mechanical sutures into tissue to be sutured. A movable leg is slidably mounted in the channel of the fixed leg and includes a lower anvil which cooperates with the head of the fixed body to close sutures which are discharged from the head. A threaded engagement is established in the fixed leg body for threadably engaging an upper part of the movable leg for moving the movable leg with respect to the fixed leg. The head of the fixed leg comprises a frame which houses a pusher for the suturing mechanism, the pusher having a shaft which is movable parallel to the movable leg and which is connected to a release mechanism for lower and raising the pusher. A V-shaped blade is movable with the pusher for performing a biopsy. The shape of the blade, the frame and the anvil are selected to remove tissue having the appropriate shape.

7 Claims, 9 Drawing Figures

SURGICAL INSTRUMENT FOR PRACTICING MECHANICAL SUTURES AND BIOPSIES

FIELD AND BACKGROUND OF THE INVENTION

The present invention refers to a novel surgical instrument for practicing mechanical suturing and biopsies, whereby suturing takes place using metal clips so that the suture has two forward-converging sides forming an inverted V and the tissue comprised between both legs is simultaneously cut and removed for analysis.

SUMMARY OF THE INVENTION

It is mainly applicable in choled cho-duodenal suturing, utilizing an instrument having about 3 cms. of suture, inserted transduodenally through the papilla. Due to the special shape thereof, terminating in a blunt point, it is suitable for other anastomoses in which the canalization of a snall orifice is necessary, such as in some cases of intestinal duplicature or transgastric cystogastrotomy, stenosis plasty, etc.

The obtention of a tissue fragment automatically and hemostatically is useful for some biopsies, such as pulmonary, genital, lymphofatty tissue, retroperitoneal, etc.

The instrument mainly comprises two legs, one of which slides inside the other. The fixed leg has a posterior channel along which the movable leg moves. The fixed leg has an upper end or body, a lower part or head for housing the suturing mechanism, and an intermediate part or rod for linking both.

DESCRIPTION OF THE PREFERRED EMBODIMENTS

Figure 1:
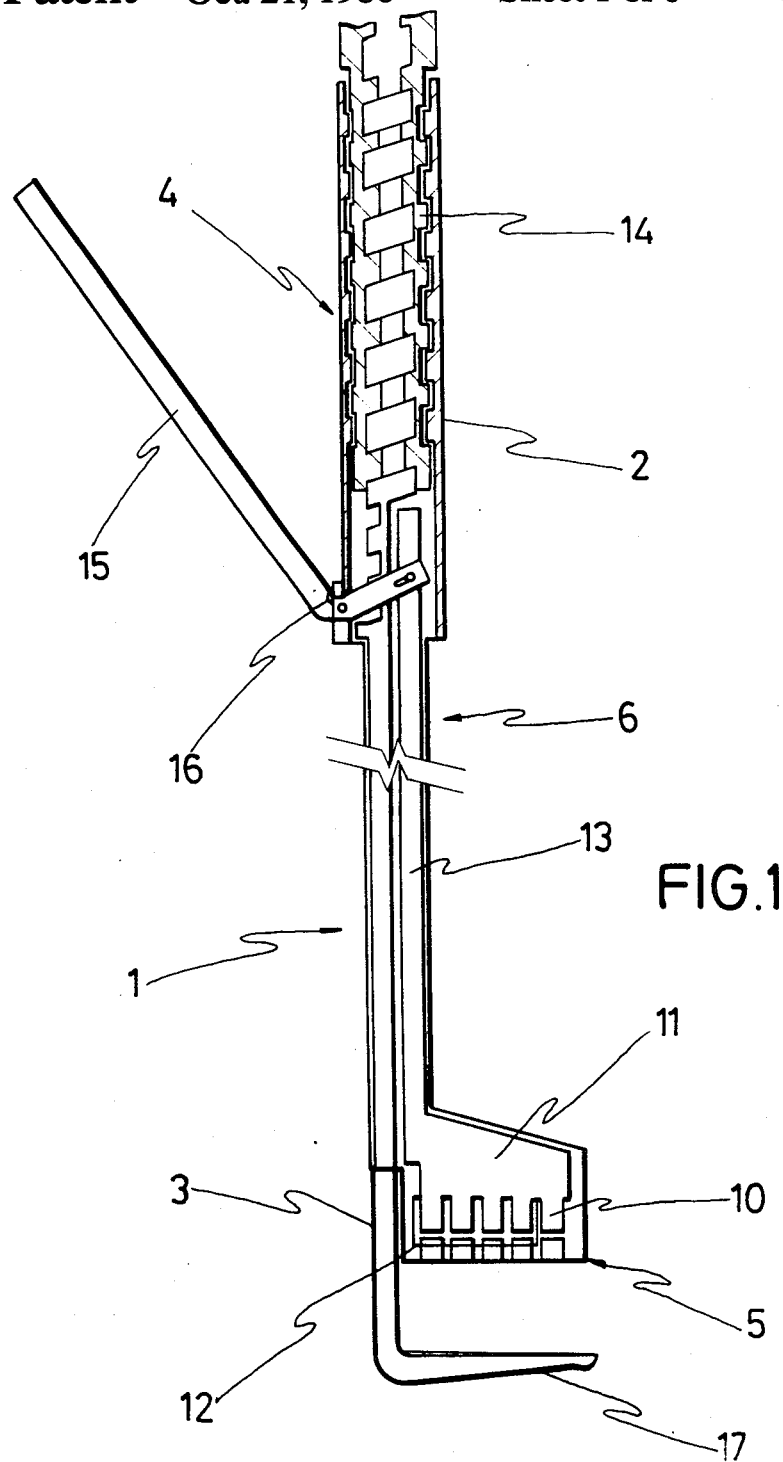
FIG. 1 represents a side elevational view of the instrument, illustrating a nut for permitting the movable leg to slide inside the fixed leg.
Figure 2:
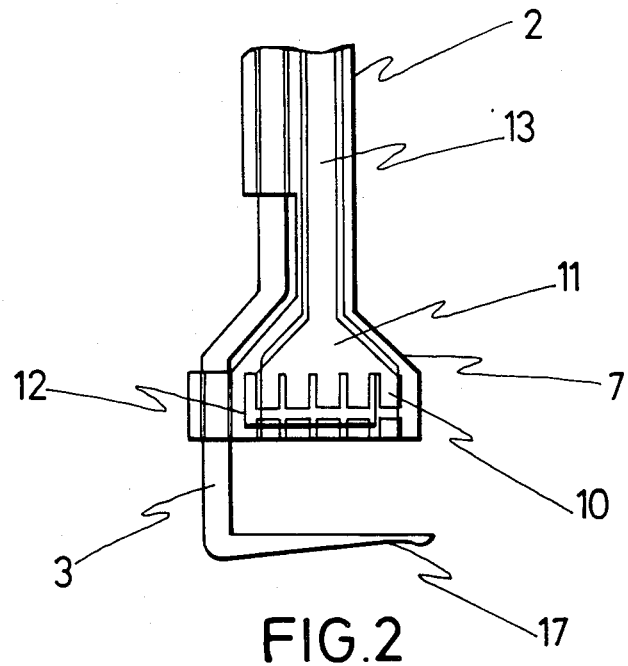
FIG. 2 represents the T-shaped head of the instrument, specially suitable for large size models.

The instrument for practicing mechanical suturing and biopsies generally designated 1 in FIG. 1, is essentially comprised of a fixed leg 2, having a posterior channel in which the movable leg 3 moves. The fixed leg 2 has an upper end or body 4, a lower part or head 5 for housing the suturing mechanism, and an intermediate part or rod 6 for linking both.

Figure 3:
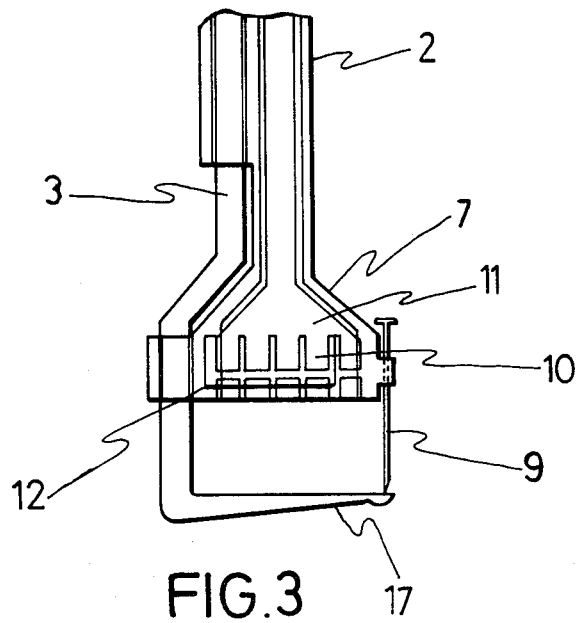
FIG. 3 represents the T-shaped head of the instrument incorporating a slidable or threaded anterior guide to increase stability.
Figure 5:
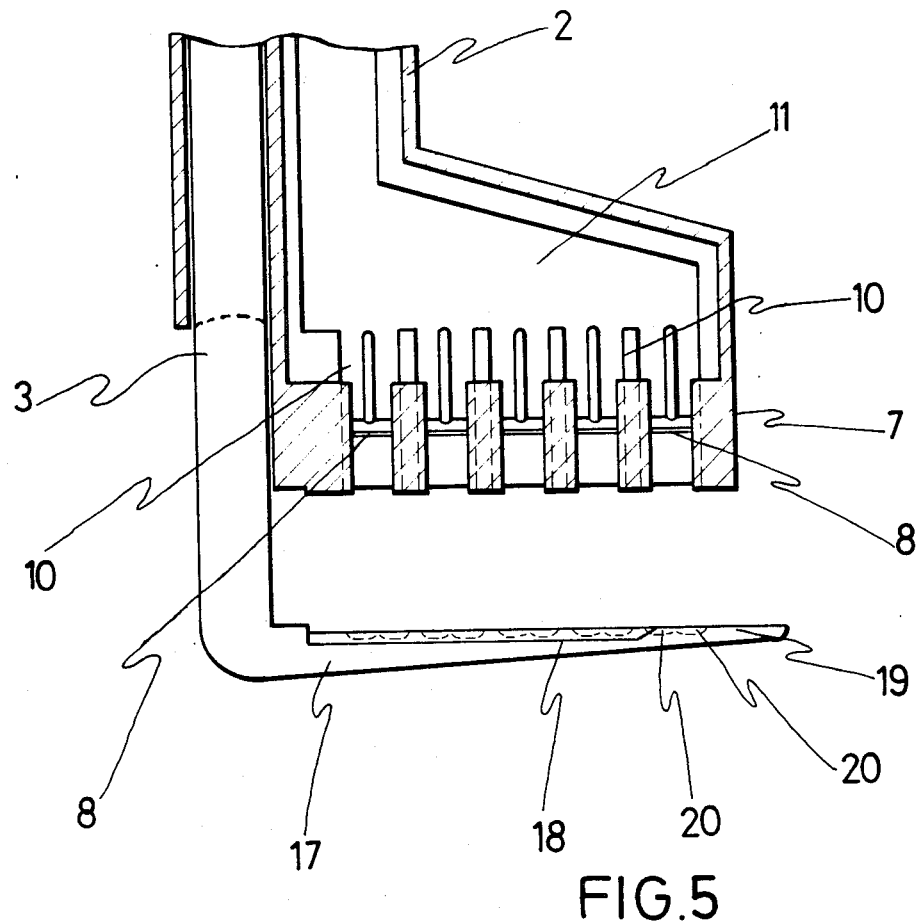
FIG. 5 illustrates an elevational view of the arrangement of the inner face of the stapling head, illustrating the staples and the pusher.
Figure 7:
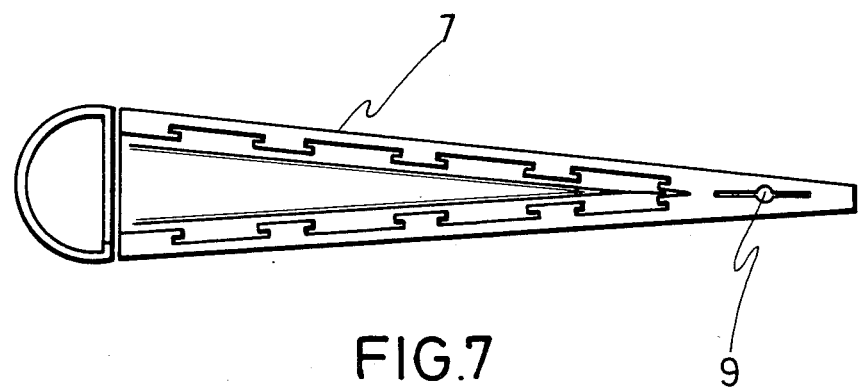

The head or suturing mechanism 5 has an irregular pyramidal or truncated pyramidal shape, the lower base of which is triangular, as illustrated in FIG. 7. The head assembly in turn has a fixed part or frame 7, in the lower edge of which the staples 8 are housed in recesses forming position means for the staples (FIG. 5). These staples are positioned downwardly, arranged in one or two rows along each of the symmetrical sides of the triangle, and approximately 1 mm. from the outer edge. They are near or at a face of the frame 7 shown in FIG. 7. The staples 8 can have a length of from 2 to 4 mm. arranged longitudinally and are spaced apart by 0.5 to 1 mm., depending on the size thereof, beginning at about 2 mm. from the posterior base and ending 2 mm. from the anterior point. The embodiment being described incorporates five staples per side, the staple of the anterior edge being common, wherefore the assembly has a total of 9 staples. The stapling head 5 can have a slidable or threaded anterior guide 9 (FIG. 3) to increase the stability of the instrument when triggered. The shape of the stapling head can, in turn, vary to adapt itself to the different functions, including the degree of opening of the V from 1° to 359°, the use of and inverted U-shape and the use of a circular or elliptical arc segment.

Above each staple 8, the recess of the frame is prolonged to receive a small element 10 having the same width as, but slightly longer than, the staple. All these elements 10 (nine of them in this case) are secured at their upper part to another element having a triangular base smaller than the frame 7, in the interior of which it is housed and guided. The assembly of elements 10 and the triangular element forms a single pusher 11, whose descent pushes the staples out of their housings. The pusher 11 incorporates, parallel and close to the row of nine elements 10, a V-shaped blade 12, open towards the part of the instrument. The edge of the blade 12 is so positioned that when the pusher 11, through its nine elements 10, contacts the staples 8, it reaches the mid point thereof. Both the pusher and the blade are shifted together and once the staples are closed, it cuts the intermediate tissue.

The intermediate part or rod 6 is merely a rigid or flexible shank forming a body with the frame, inside which and at the back the movable leg 3 slides, while a shaft 13 joined to the pusher slides at the front. The rigid rod 6 can be straight or curved, in which case it will adopt the shape most suitable for the function for which it has been designed. In the preferred embodiment of this invention (choledocho-duodenostomy), the most favourable curvatures will be towards the right, backwards or preferably mixed, curves of up to 90° being acceptable. The average length of the rod 6 can range from about 5 to about 30 cm. although from 15 to 20 cm. is considered as the ideal size. The flexible rod is preferably suitable for small size models, for papilloplasty or biopsy.

The upper end or body 4 is the zone at which the instrument incorporating the conventional mechanisms permitting use thereof is joined. The first of these mechanisms, i.e. approximation mechanism, is comprised of a frame or fixed part, common to the entire instrument which at its upper end is mounted with a screw 14 turning freely therein. The screw 14 is internally threaded to mesh in turn with the movable leg 3 to form slide means therefore. The shape of the movable leg at this point is screw-like, wherefore the turn of the screw 14 will determine its axial displacement. The second mechanism, i.e. trigger mechanism, comprises a release 15, an element having an angle of about 90° hinged to the fixed leg close to its inflection by means of a scissor mechanism. The short side of the mentioned release penetrates into the body of the apparatus to be hinged to the shaft 13 of the pusher by means of a slidable pin. The release 15 can incorporate a safety mechanism to prevent the accidental closure thereof, consisting of a pin 16 close to the articulation at the outer side.

Figure 6:
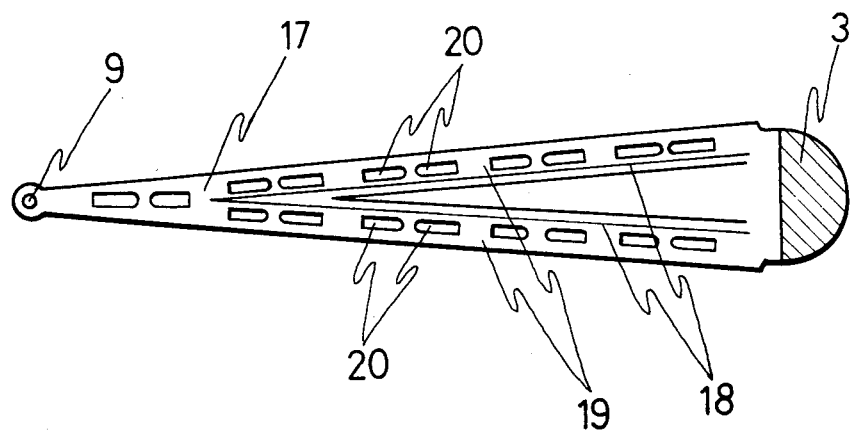
FIGS. 6 and 7 represent the upper face of the anvil of the movable leg and the lower face of the stapling head, respectively, between which the tissue to be sutured and cut is held. The centre zone thereof will be retained inside the V of the blade.

The movable leg 3 has two parts, a longitudinal part housed in the posterior channel of the leg 2, the upper end of which is screw-shaped. At the lower end it makes a curve of 90°, giving rise to the transversal part or anvil 17 which reproduces the shape of the lower face of the stapling head, the same triangular shape, increasing slightly towards the anterior edge which, in this case, has a thickening. Its upper face 19, illustrated in FIG. 6, is provided with grooves 20 for the closure of the staples 8, the number thereof corresponding to the number of staples, nine in all. At 1 mm. from the inner edge of the grooves, there is an inverted V-shaped recess 18 for receiving the blade. The lower face is hemiconical, the point being thickened forwards. This thickening can have a central hole if the head has an anterior guide 9.

FIG. 7 shows the triangular lower face of the fixed frame with the V-shaped blade. The V-shaped blade has two blade portions which converge to a pointed apex shown at the right in FIG. 7 and which have bases shown at the left in FIG. 7 that are spaced from each other so that an open V-shaped cut can be formed when the blade is pushed against the V-shaped recess is shown in FIG. 6 with tissue position between the blade and the recess.

The instrument functions as follows: In an open position, i.e. separating the anvil 17 from the head frame 7, and once the duodenum is open with a small hole and the papilla is visible, the thickening of the anvil is inserted through the hole thereof. The size and shape described facilitate this operation. At the same time, due to the progressively increasing section, the insertion thereof in the papilla is not traumatic, producing a smooth expansion of the papilla without breakage. With the correct and complete insertion of the anvil 17, the entire sphincteral mechanism (papillar sphincter and choledocyano itself) is positioned thereon, as well as the discal sector of the rectropancreatic choledocho. Its incomplete insertion will determine minor forms of anastomoses superpositionable to manual papilloplasties.

Once the anvil 17 is inserted in the discal biliary tract, the head 5 is brought closer, causing the upper screw 14 of the fixed leg 2 to turn until it reaches a determined butt. At this moment, the pin 16 is removed from the release.

The release means 15 is then brought closer to the fixed leg 2 until it is completely closed. If the anvil 17 has been correctly positioned following the axis of the smaller duodenal curvature and the head has been positioned vertical thereto, the anastomosis would have taken place with a small amount of intermediate tissue. The staples 8 are closed on the anvil 17 through the joined duodenal and choledocyano walls, causing the inverted V-shaped suture. Immediately thereafter the blade 12 cuts the intermediate tissue, also in the shape of an inverted V, establishing the anastomosis between the choledocho and the duodenum.

By activating the release 15, the leg thereof is raised and the anvil is separated from the head when turning the upper screw in an opposite direction. Finally, the instrument is removed, the anastomosis (haemostasia of the eges and integrity of the pancreatic orifice) is verified and the tissue comprised in the V of the blade is removed for examination and analysis. The anvil adapts itself to the upper face, following the morphological variations thereof. In large size models, the back portion can be open to favour removal of the piece.

Figure 4:
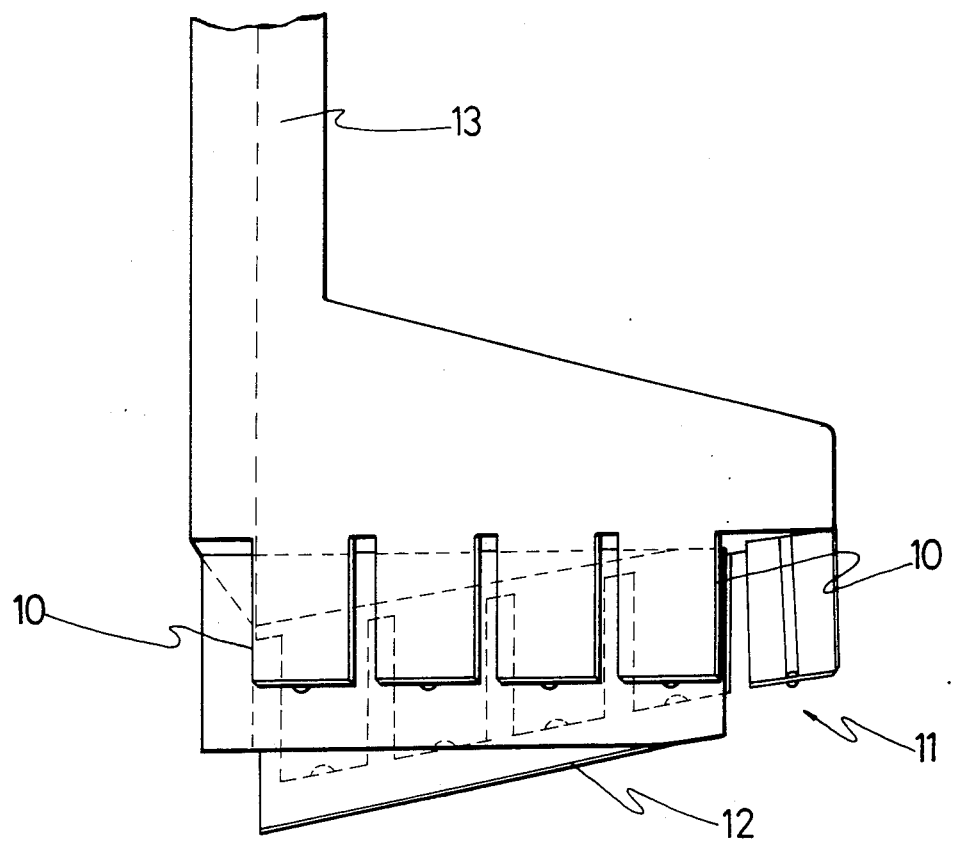
FIG. 4 represents a perspective view of the pusher housed in the head of the stapler, illustrating the triangular-based truncated pyramidal arrangement and the cutting blade.

FIG. 4 shows that the elements 10 have a rectangular cross-section and are arranged in a V-shape with blade 12 inside the V-shape.

The procedure is similar for other applications.

Some of the advantages presented by the instrument of the invention are:

A biliodigestive anastomosis can be practised automatically for the first time.

A biopsy of the allegedly pathologic tissue can be taken simultaneously.

Anastomosis is rapid, the operation time being highly reduced.

Anastomosis is safe and hemostatic, the technical errors made when operating a readily bleedable, small and deep zone are avoided.

Anastomosis is easy, and a delicate and risky technique for any surgeon in any situation is readily available.

It presents the advantage of anastomoses in biliodigestive continuity, preventing the syndrome of residual or blind choledochal stump.

The correct application thereof does not affect the pancreatic tract.

The instrument can have other applications. In principle, all kinds of transvisceral anastomoses, such as transgastric cystogastrotomy or cystoenterostomy of the intestinal duplicature or enlargement of the digestive or biliodigestive fistulae through a small orifice to be canalized and moderately expanded, or plasty of stegnosis.

Figure 8:
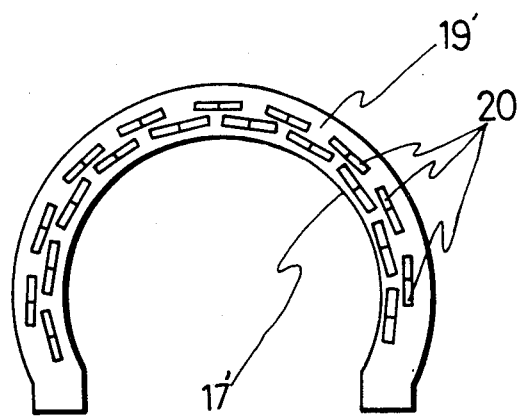
FIGS. 8 and 9 represent the upper face of the anvil and the lower face of the stapling head, respectively, specially designed for practising pulmonary biopsies.
Figure 9:
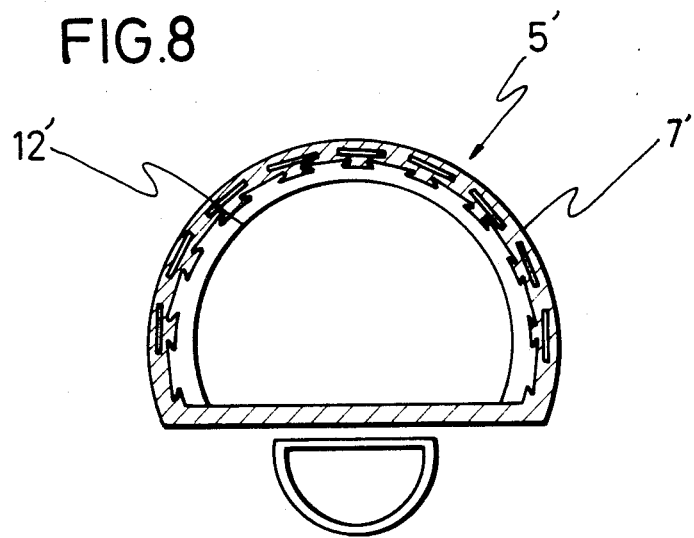

The different sizes and openings of the V permit biopsies to be practised rapidly and hemostatically, especially pulmonary biopsies, without the intervention of other instruments. Rounded rows and points (FIGS. 8 and 9) can be recommendable in cases of pulmonary biopsies. Likewise, tissues difficult to locate or requiring haemostasis, suh as ganglions and retroperitoneal lymphofatty tissue or genital are also fields of use. In FIGS. 8 and 9 the same reference numerals are used with a prime to denote similar parts with numeral 20 denoting grooves that are the same as grooves 20 in anvil 17 of FIG. 6.

I claim:

1. A surgical instrument for placing suture staples and performing biopsies, comprising:

a fixed leg having an upper body and a lower body connected to said upper body, said upper body defining a channel and said lower body comprising a fixed frame, said frame having a lower triangular face and positioning means for arranging a plurality of suture staples in a V-shaped configuration adjacent said face, said triangular face including openings for staples in said positioning means;

a movable leg slidably engaged in said channel and having a triangular anvil movable toward and away from said triangular face of said fixed frame, said anvil having an upper triangular surface for interaction with and the closing of staples from said frame, and a blunt end;

slide means in said upper body between said fixed leg and said movable leg for sliding said movable leg with respect to said fixed leg;

a staple pusher movably mounted in said lower body of said fixed leg for pushing staples out of said positioning means into engagement with said triangular surface of said anvil;

release means engaged with said fixed leg and connected to said staple pusher for moving said staple pusher; and a V-shaped cutting blade conencted to and movable with said staple pusher beyond said face of said frame for cutting tissue between said frame face and said anvil surface, said openings for staples in said face of said frame being disposed outwardly of said V-shaped blade, said blade having two conveying blade portions converging to an apex where said blade portions meet, said blade portions having bases opposite from said apex which are spaced from each other, whereby an open cut is formed by said blade.

2. A surgical instrument according to claim 1, wherein said pusher has a lower triangular configuration and carries a plurality of rectangular pushing elements disposed in a triangular configuration for pushing staples from said positioning means.

3. A surgical instrument according to claim 2, wherein said surface of said anvil includes a plurality of recesses lying in a V-shaped configuration for receiving and closing staples from said positioning means, said surface of said anvil including a further V-shaped recess for receiving said blade which is positioned inwardly of said recesses for receiving staples from said positioning means.

4. A surgical instrument according to claim 3, wherein said slide means comprising a screw rotatably mounted at a fixed position in said upper body, said movable leg having an upper part with an external thread threadably engaged in said screw for movement of said movable leg with rotation of said nut.

5. A surgical instrument according to claim 4, wherein said release means comprises a lever pivotally mounted to said upper body and having an arm, said staple pusher including a shaft slidably mounted in said upper body and connected to said arm.

6. A surgical instrument according to claim 5, including a release pin engaged with said lever for holding said lever in a position to maintain said staple pusher away from said positioning means for staples.

7. A surgical instrument according to claim 6, wherein said positioning means comprises an arrangement or recesses, each recess for receiving a staple, said pusher elements being shaped to be receivable in each of said recesses respectively with downward movement of said staple pusher for discharging staples from said recesses and into engagement with said surface of said anvil.

* * * * *